United States Patent
Marini et al.

(10) Patent No.: US 10,596,090 B2
(45) Date of Patent: Mar. 24, 2020

(54) COSMETIC FORMULATION TO REDUCE FACIAL FLUSHING

(71) Applicant: Jan Marini Skin Research, San Jose, CA (US)

(72) Inventors: Jan Marini, San Jose, CA (US); Subhash J. Saxena, Ringoes, NJ (US)

(73) Assignee: Jan Marini Skin Research, San Jose, CA (US)

( * ) Notice: Subject to any disclaimer, the term of this patent is extended or adjusted under 35 U.S.C. 154(b) by 569 days.

(21) Appl. No.: 15/167,332

(22) Filed: May 27, 2016

(65) Prior Publication Data
US 2017/0340554 A1    Nov. 30, 2017

(51) Int. Cl.
| | | |
|---|---|---|
| *A61K 36/82* | (2006.01) |
| *A61K 36/00* | (2006.01) |
| *A61K 36/48* | (2006.01) |
| *A61K 36/71* | (2006.01) |
| *A61K 8/46* | (2006.01) |
| *A61K 8/362* | (2006.01) |
| *A61K 8/64* | (2006.01) |
| *A61K 8/41* | (2006.01) |
| *A61K 8/49* | (2006.01) |
| *A61K 8/34* | (2006.01) |
| *A61Q 19/00* | (2006.01) |
| *A61K 8/9789* | (2017.01) |

(52) U.S. Cl.
CPC .......... *A61K 8/46* (2013.01); *A61K 8/34* (2013.01); *A61K 8/362* (2013.01); *A61K 8/411* (2013.01); *A61K 8/498* (2013.01); *A61K 8/4946* (2013.01); *A61K 8/64* (2013.01); *A61K 8/9789* (2017.08); *A61Q 19/007* (2013.01); *A61K 2800/70* (2013.01)

(58) Field of Classification Search
None
See application file for complete search history.

(56) References Cited

U.S. PATENT DOCUMENTS

| | | |
|---|---|---|
| 6,821,524 B2 | 11/2004 | Marini |
| 8,318,678 B2 | 11/2012 | Marini |
| 2007/0196318 A1 | 8/2007 | Marini |
| 2009/0263513 A1 | 10/2009 | Marini |
| 2010/0021571 A1 * | 1/2010 | Waugh ................ A61K 31/192  424/747 |
| 2010/0247693 A1 | 9/2010 | Marini |
| 2013/0189211 A1 | 7/2013 | Marini |
| 2014/0228291 A1 | 8/2014 | Subhash et al. |
| 2017/0035687 A1 * | 2/2017 | Dhar ..................... A61K 35/12 |

FOREIGN PATENT DOCUMENTS

| | | | |
|---|---|---|---|
| EP | 1203579 A1 | 5/2002 | |
| EP | 1369107 A1 | 12/2003 | |
| EP | 1825845 A1 | 8/2007 | |
| WO | 2009/148551 A1 | 12/2009 | |
| WO | WO-2012177433 A1 * | 12/2012 | ........... A61K 31/194 |
| WO | WO-2014011875 A1 * | 1/2014 | ......... A61K 41/0071 |

* cited by examiner

*Primary Examiner* — Michael Barker
(74) *Attorney, Agent, or Firm* — Pamela J. Sherwood; Bozicevic, Field & Francis LLP

(57) ABSTRACT

The present invention features novel cosmetic skin care compositions for improving the appearance of flushed or rosacea-affected skin.

6 Claims, 1 Drawing Sheet
(1 of 1 Drawing Sheet(s) Filed in Color)

COSMETIC FORMULATION TO REDUCE FACIAL FLUSHING

BACKGROUND OF THE INVENTION

Rosacea is a common but often misunderstood condition that is estimated to affect over 45 million people worldwide. There are several symptoms and conditions associated with rosacea. These include frequent flushing, vascular rosacea, inflammatory rosacea, and several other conditions involving the skin, eyes, and nose. Frequent flushing of the center of the face, which may include the forehead, nose, cheeks, and chin, occurs in the earliest stage of rosacea. The flushing often is accompanied by a burning sensation, particularly when creams or cosmetics are applied to the face. Rosacea sufferers often report periods of depression stemming from cosmetic disfigurement, painful burning sensations, and decreases in quality of life.

Vascular rosacea causes persistent flushing and redness. Blood vessels under the skin of the face may dilate, showing through the skin as small red lines. This is called telangiectasia. The affected skin may be swollen slightly and feel warm. Inflammatory rosacea causes persistent redness and papules (pink bumps) and pustules (bumps containing pus) on the skin. Eye inflammation and sensitivity as well as telangiectasia also may occur.

In the most advanced stage of rosacea, the skin becomes a deep shade of red and inflammation of the eye is more apparent. Numerous telangiectases are often present, and nodules in the skin may become painful. A condition called rhinophyma also may develop in some men; it is rare in women. Rhinophyma is characterized by an enlarged, bulbous, and red nose resulting from enlargement of the sebaceous (oil-producing) glands beneath the surface of the skin on the nose. People who have rosacea also may develop a thickening of the skin on the forehead, chin, cheeks, or other areas.

In addition to skin problems, many people who have rosacea have eye problems caused by the condition. Typical symptoms include redness, dryness, itching, burning, tearing, and the sensation of having sand in the eye. The eyelids may become inflamed and swollen. Some people say their eyes are sensitive to light and their vision is blurred or otherwise impaired.

Factors that may cause rosacea to flare up may include heat (including hot baths), strenuous exercise, sunlight, wind, very cold temperatures, hot or spicy foods and drinks, alcohol consumption, menopause, emotional stress, long-term use of topical steroids on the face, and bacteria.

Cosmetic compositions that calm the skin and reduce flushing, including rosacea, are of great interest and are provided herein.

SUMMARY OF THE INVENTION

Cosmetic compositions are provided that reduce facial flushing and calm the skin. In some embodiments, the flushing or redness is associated with rosacea. Specifically, the skin care compositions presented herein contain a synergistic combination of anti-redness agents azelaic acid, tetrapeptide-14 and *Ranunculus ficaria* extract; combined with a combination of herbal extracts with skin calming properties, including oat extract, a blend of tea extracts, which may comprise green tea, red tea and white tea extracts; and *Boswellia serrata* extract, and allantoin acetyl methionine, for use in improving the appearance of flushed or rosacea-affected regions of the skin. The formulation is provided in a cosmetically acceptable vehicle(s), for example as a lotion. Accordingly, the combinations of the active ingredients of the invention are formulated as skin care cosmetic compositions that can be applied directly to the skin so as to improve the appearance of skin texture and color. The compositions may additionally provide cosmetic benefit for acne, discoloration, oily skin, aging skin, spider veins, and sun damage.

According to the first aspect of the invention, there is provided a cosmetic composition comprising an effective dose of azelaic acid, tetrapeptide-14 and *Ranunculus ficaria* extract; combined with skin calming extracts. On some embodiments the extracts comprise oat extract; tea extracts, e.g. green tea, red tea and white tea extracts; *Boswellia serrata* extract, and allantoin acetyl methionine, for use in improving the appearance of flushed or rosacea-affected regions of the skin.

In the second aspect of the invention, a method is provided for improving the appearance of flushed or rosacea-affected regions of the skin, the method comprising applying topically a cosmetic formulation comprising an effective dose of azelaic acid, tetrapeptide-14 and *Ranunculus ficaria* extract; combined with skin calming extracts. On some embodiments the extracts comprise oat extract; tea extracts, e.g. green tea, red tea and white tea extracts; *Boswellia serrata* extract, and allantoin acetyl methionine. The composition is topically administered as a lotion or cream for a period of time sufficient to accomplish the desired effect. In some embodiments the composition is administered once daily, or twice daily, and for at least about one week, at least about two weeks, at least about one month, or longer as desired.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1A:
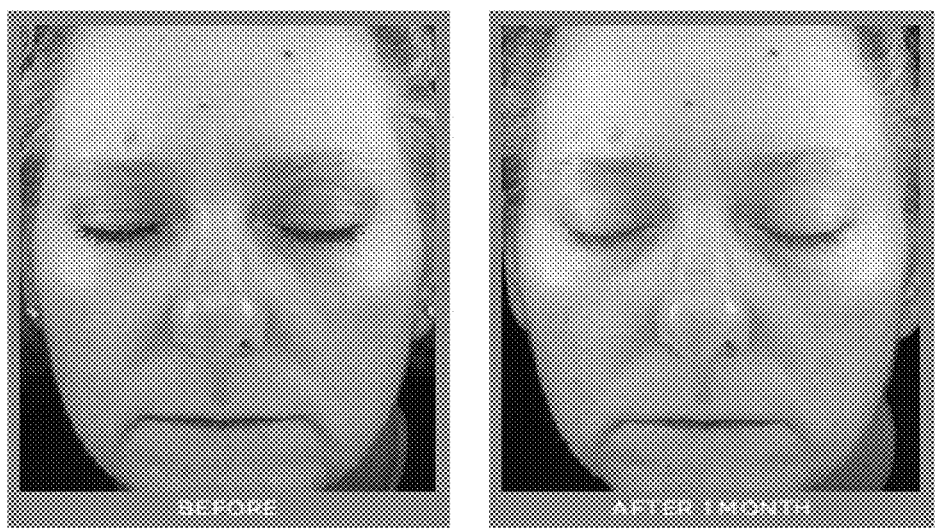
FIGS. 1A, 1B and 1C show the results of use of Rosalieve™ face lotion. The lotion was applied twice daily for one month. The results show a dramatic change in skin tone after regular use of the product.
Figure 1B:
Figure 1C:

Topical compositions are provided for improving the appearance of the flushing or redness of skin, which can include redness associated with rosacea. The compositions may additionally provide cosmetic benefit for acne, discoloration, oily skin, aging skin, spider veins, and sun damage.

Components of the Cosmetic Compositions

Azelaic acid is a saturated dicarboxylic acid that is produced by *Malassezia furfur*, a yeast that lives on normal skin. When applied topically to the skin in a combination formulation it acts synergistically with the other agents of the of the invention. The cosmetic compositions of the present invention may contain azaleic acid in amounts that are safe and effective, for instance, at concentrations of at least about 0.05%, at least about 0.5%, around about 2%, around about 5%, and usually not more than about 10% (weight/weight).

Tetrapeptide-14 is a 4 amino acid peptide, usually in amidated form (CAS 1143505-63-8 and commercially available from Grant Enterprises, see U.S. Pat. No. 8,071,555, herein specifically incorporated by reference). The peptide can be amidated, lipidated or conjugated to a carrier molecule. As used herein, "peptides" refers to both naturally occurring peptides and synthesized peptides.

Such peptides can be acylated, comprising at least one lipid moiety, which moiety may be myristoyl, palmitoyl, etc., which increases the hydrophobicity of the peptide. Myristoyl or palmitoyl pentapeptides are of particular interest, as is the use of thymosin β4. Below is a non-limiting list of exemplary peptide agents that find use in the cosmetic compositions of the present invention. The peptide is a competitive inhibitor of TRAF6 binding, which blocks the transmission of the inflammatory signal and hence reduce the inflammatory response. Such tetrapeptides reduce the amount of interleukin (IL)-6 and matrix metalloproteinase (MMP)-1 expressed by skin epithelial and fibroblast cells in response to ultraviolet light (UV) exposure.

Tetrapeptide-14 is provided in the compositions of the invention at a concentration (wt/wt) of at least about 0.0005%, up to about 0.01%, and may be provided at a concentration of around about 0.00075 to about 0.0025%, or around 0.001%.

Allantoin acetyl methionine, (CAS4207-40-3) is a skin protectant agent with keratolytic, moisturizing, soothing and healing properties. It is provided in the compositions of the invention at a concentration of from about 0.05% to about 1%, and may be provided at a concentration of from about 0.1% to about 0.5%, or around about 0.2% by weight.

A blend of herbal extracts in the composition provide anti-oxidants and skin calming agents. Extracts from teas, oat, *Boswellia serrata* and *Ranunculus ficaria* may be included. Tea extracts can include extracts of *Camellia sinensis, Camellia oleifera* and *Aspalathus linearis*. Tea extracts contain polyphenols with antioxidant and anti-inflammatory properties.

Epigallocatechin-3-gallate (EGCG, CAS 989-51-5), an extract of green tea is the ester of epigallocatechin and gallic acid, and is a type of catechin. It is found in high content in the dried leaves of tea. The present formulations contain a concentration that is useful in soothing the skin, as well as reducing the appearance of fine lines and wrinkles. Epigallocatechin-3-gallate is provided in the compositions of the invention at a concentration of at least about 0.01% to about 1%, and may be provided at a concentration of from about 0.05% to about 0.5%, or around about 0.1%.

*Camellia sinensis* extract (white tea, CAS 84650-60-2) is provided in the compositions of the invention at a concentration of from about 0.005% to about 0.1%, and may be provided at a concentration of from about 0.01% to about 0.05%, or around about 0.02% by weight.

*Aspalathus linearis* extract (red tea, CAS 6027-43-6) is provided in the compositions of the invention at a concentration of from about 0.005% to about 0.1%, and may be provided at a concentration of from about 0.01% to about 0.05%, or around about 0.0325% by weight.

*Boswellia serrata* extract (CAS 97952-72-2) is derived from a gum resin extracted from a tree. The extracts, via active boswellic acids, have potent anti-inflammatory activity, including inhibition of 5-lipoxygenase and NF-κB. The extract is provided in the compositions of the invention at a concentration of from about 0.005% to about 0.1%, and may be provided at a concentration of from about 0.01% to about 0.05%, or around about 0.0125% by weight.

Oat extract (hydroxyphenyl propamidobenzoic acid, CAS 697235-49-7) is an anti-irritant that calms the skin. It is provided in the compositions of the invention at a concentration of from about 0.005% to about 0.1%, and may be provided at a concentration of from about 0.01% to about 0.05%, or around about 0.03% by weight.

*Ranunculus ficaria* extract is a botanical extract that soothes and calms irritated skin while reducing redness. It contains phenolic derivatives such as rutin and tri-terpenic saponins that help decongest skin tissue and reduce blotchiness. (CAS 84929-74-8, commercially available from Gattefosse). *Ranunculus ficaria* extract is provided in the compositions of the invention at a concentration (wt/wt) of at least about 0.05%, up to about 1%, and may be provided at a concentration of about 0.25% to about 0.75%, or around 0.5%.

In addition to the combination of agents listed, the cosmetic formulation may include other active agents. In some embodiments, the formulation comprises permeation enhancer, e.g. transcutol, (diethylene glycol monoethyl ether), which may be provided at a weight/weight concentration of from about 0.1% to about 10%, usually from about 2.5% to about 7.5%, more usually about 5%.

Skin Soothing/Conditioning Agents

The cosmetic compositions of the present invention may contain agents that sooth, condition and/or heal the skin and hair. These include estradiol; progesterone; pregnanalone; coenzyme Q10; methylsolanomethane (MSM); copper peptide (copper extract); plankton extract (phytosome); kojic acid; ascorbyl palmitate; all-trans-retinol; broparoestrol; estrone; adrostenedione; androstanediols; etc. The steroids will generally be present at a concentration of less than about 5% or about 10% of the total by weight of the composition, while the other skin benefit materials may be present at higher levels, for example as much as about 10 to about 15%.

The compositions may further comprise sunscreens to lower skin's exposure to harmful UV rays. Sunscreens include those materials commonly employed to block ultraviolet light. Illustrative compounds are the derivatives of PABA, cinnamate and derivatives of salicylate (other than ferulyl salicylate). For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. Dermascreen may also be used. The exact amount of sunscreen employed in the compositions can vary depending upon the degree of protection desired from the sun's UV radiation.

The amounts of cosmetic or dermatological auxiliaries and additives and perfume to be used in each case can easily be determined by simple exploratory experiments by the person skilled in the art, depending on the nature of the product in question.

Cosmetically Acceptable Vehicle

The compositions of the invention include a cosmetically acceptable vehicle to act as a diluent, dispersant or carrier for the active agents, so as to facilitate distribution and uptake when the composition is applied to the skin. Vehicles other than or in addition to water can include liquid or solid emollients, solvents, humectants, thickeners and powders.

The cosmetically acceptable vehicle will usually form 5% to 99.9%, preferably from 25% to 80% by weight of the composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase (O/W) or conversely (W/O); or suspensions or emulsions of smooth, semi-solid or solid consistency of the cream or gel type. These compositions are formulated according to the usual techniques as are well known to this art.

When the compositions of the invention are formulated as an emulsion, the proportion of the fatty phase may range from 5% to 80% by weight, and preferably from 5% to 50% by weight, relative to the total weight of the composition. Oils, emulsifiers and co-emulsifiers incorporated in the composition in emulsion form are selected from among those used conventionally in the cosmetic or dermatological field. The emulsifier and co emulsifier may be present in the composition at a proportion ranging from 0.3% to 30% by weight, and preferably from 0.5% to 20% by weight, relative to the total weight of the composition.

When the compositions of the invention are formulated as an oily solution or gel, the fatty phase may constitute more than 90% of the total weight of the composition.

The compositions of the invention may be in the form of body cleansing compositions. As such, these compositions may contain at least one wash-active surfactant in an aqueous base are preferred embodiments of the invention. The surfactants can be present, alone or in a mixture, and are contained in an amount of preferable from 1 to 50% by weight, especially preferably from 1 to 30% by weight. Nonionic surfactants, amphoteric surfactants, zwitterionic surfactants and anionic surfactants are generally suitable.

Suitable anionic surfactants include, e.g. alkaline or alkaline earth salts, alpha-olefin sulfonates, sulfosuccinates, disodium laureth-3 sulfosuccinate, disodium PEG-5 lauryl citrate sulfosuccinate, disodium ricinolamido MEA-sulfosuccinate or disodium laurylamido MEA-sulfosuccinate and alkyl ether carboxylates.

Suitable nonionic surfactants include e.g. alkoxylated fatty alcohols, alkoxylated fatty acid esters, alkoxylated partial glycerides, saturated or unsaturated fatty acids, alkoxylated polyol esters, and alkylpolyglucosides, such as coconut glucosides, lauryl glycosides or decylglucosides. For example, ethoxylated lauryl alcohol, tetradecyl alcohol, cetyl alcohol, oleyl alcohol or stearyl alcohol, which are used alone or in mixtures with each other, as well as fatty alcohols of ethoxylated lanolin, are suitable as fatty alcohol ethoxylates. Furthermore the ethoxylated fatty acid sugar esters known as nonionic surfactants, especially ethoxylated sorbitan fatty acid ester, are suitable for use in the cosmetic preparations according to the invention. The suitable ethoxylated fatty acid sugar esters include those marketed under the trade names Tween™ and Arlacel™ by ICI surfactants and the alkyl-polyglycosides, which are marketed under the trade names Plantaren™ or Plantacare™ by Henkel or under the trade name Oramix™ by Seppic.

Suitable amphoteric surfactants include for example betaines, such as cocoamidopropylbetaine or lauryl betaine, sulfobetaines, such as cocoamidopropyl hydroxysultaine, glycinates, such as cocoamphoglycinate (INCI-name: sodium cocoamphoacetate) and diglycinates and propionates, such as cocoampho-propionate.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the field, and, for example, range from 0.01% to 10% of the total weight of the composition. Depending on their nature, these additives and adjuvants may be introduced into the fatty phase or into the aqueous phase.

Exemplary oils which may be used according to this invention include mineral oils (liquid petrolatum), plant oils (liquid fraction of karite butter, sunflower oil), animal oils (perhydrosqualen(e), synthetic oils (purcellin oil), silicone oils (cyclomethicone) and fluoro oils (perfluoropolyethers). Fatty alcohols, fatty acids (stearic acid) and waxes (paraffin wax, carnauba wax and beeswax) may also be used as fats.

Emulsifiers which may be used include glyceryl stearate, polysorbate 60, PEG-6/PEG-32/glycol stearate mixture, etc. Solvents which may be used include the lower alcohols, in particular ethanol and isopropanol, and propylene glycol.

Hydrophilic gelling agents include carboxyvinyl polymers (carbomer), acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Compositions of the invention may be applied to any subject and used to treat a variety of conditions, for example skin redness associated with rosacea, e.g. in rosacea telangiectasia, and papulopustular rosacea. The compositions may additionally provide cosmetic benefit for acne, discoloration, oily skin, aging skin, spider veins, and sun damage. A typical composition of the invention is formulated as a solution, lotion, cream, gel, ointment, liniment, solvent, emulsion, dispersion, hydrodispersion, aerosol, propellant, soap, exfoliant or transdermal patch, which may be applied topically to the skin so as to treat, prevent, wash, condition or otherwise effect a condition of the skin.

Product Use, Form, and Packaging

In use, a quantity of the composition, for example from 1 to 100 ml, is applied to a site of interest from a suitable container or applicator and, if necessary, it is then spread over and/or rubbed into the site using the hand or fingers or a suitable device. The product may be specifically formulated for use as a treatment for a specific area, e.g. the hands, the face, the arms, etc.

The cosmetic composition of the invention can be formulated in any form suitable for application to the site of interest, including a lotion, cream, gel, or the like. The composition can be packaged in any suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLE 1

Example 1 illustrates a topical composition according to the present invention. The composition can be processed in conventional manner and is suitable for cosmetic use. In particular the compositions are suitable for application to a site of interest for the treatment of a variety of skin conditions.

Marini Rosalieve ™ Lotion

| CAS number | Name | Final concentration by weight |
|---|---|---|
| 123-99-9 | Azelaic acid | 0.5 to 10% |
| 1143505-63-8 | tetrapeptide 14 | 0.00075-0.0025% |
| 84929-74-8 | *Ranunculus ficaria* extract | 0.25-0.75% |
| 97952-72-2 | *Boswellia serrata* extract | 0.01-0.05% |
| 697235-49-7 | Oat Extract (hydroxyphenyl proamidobenzoic acid) | 0.01-0.05% |
| 6027-43-6 | *Aspalathus linearis* leaf extract | 0.01-0.05% |
| 84650-60-2 | *Camellia sinensis* leaf extract | 0.01-0.05% |
| 989-51-5 | Epigallocatechin gallate | 0.05-0.5% |
| 4207-40-3 | Allantoin acetyl methionine | 0.1%-0.5% |

Additional ingredients can be included to provide a cosmetically acceptable vehicle and to bring the volume to 100%, comprising one or more of water, Aloe Barbadensis (Aloe Vera) Leaf Juice, Bisabolol, Botanistat PF-64, Brij S721-PW-(AP), Butylene Glycol, Butyrospermum Parkii (Shea Butter), Caprylic/Capric Triglyceride, Caprylyl Glycol, Cetyl Alcohol, Citric Acid*, Dimethicone, DL-Panthenol 50L, Ethoxydiglycol, Ethylhexylglycerin, Glyceral Stearate SE, Glycerin, Hexylene Glycol, Honey Extract, Isononyl Isononanoate, Lipex Shea/BioButter Shea, U.N., Magnesium Aluminum Silicate, Panthenol, Pentylene Glycol, Phenoxyethanol, Quartz, Sodium Benzoate, Sodium Hyaluronate, Sodium PCA, Steareth-2, Tocopheryl Acetate, Xanthan Gum.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cosmetic composition for topical application comprising:
    0.05-10% by weight azelaic acid; 0.00075-0.0025% by weight Tetrapeptide-14; 0.25-0.75% by weight *Ranunculus ficaria* extract; 0.01-0.05% by weight *Boswellia serrata* extract; 0.01-0.05% by weight hydroxyphenyl proamidobenzoic acid; 0.01-0.05% by weight *Aspalathus linearis* leaf extract; 0.01-0.05% by weight *Camellia sinensis* leaf extract; 0.05-0.5% epigallocatechin gallate; 0.1%-0.5% allantoin acetyl methionine; and
    a cosmetically acceptable vehicle.

2. The composition of claim 1, further comprising a permeation enhancer at a concentration of 2.5% to 7.5%.

3. A cosmetic composition for topical application comprising:
    0.05-10% by weight azelaic acid; 0.00075-0.0025% by weight Tetrapeptide-14; 0.25-0.75% by weight *Ranunculus ficaria* extract; 0.01-0.05% by weight *Boswellia serrata* extract; 0.01-0.05% by weight hydroxyphenyl proamidobenzoic acid; 0.01-0.05% by weight *Aspalathus linearis* leaf extract; 0.01-0.05% by weight *Camellia sinensis* leaf extract; 0.05-0.5% epigallocatechin gallate; 0.1%-0.5% allantoin acetyl methionine; and a cosmetically acceptable vehicle, wherein the permeation enhancer is diethylene glycol monoethyl ether at a concentration of 2.5% to 7.5%.

4. The composition of claim 1, formulated as a lotion.

5. A method of improving the appearance of flushed or rosacea-affected skin, comprising:

topically applying a cosmetic composition of claim 1.

6. The method of claim 5, wherein the cosmetic composition is formulated as a lotion.

* * * * *